United States Patent
Okuda et al.

(10) Patent No.: US 6,845,330 B2
(45) Date of Patent: Jan. 18, 2005

(54) ELECTROMAGNETIC FLOWMETER

(75) Inventors: Kouji Okuda, Tokyo (JP); Shin Suzuki, Tokyo (JP); Ichiro Mitsutake, Tokyo (JP)

(73) Assignee: Yamatake Corporation, Tokyo (JP)

( * ) Notice: Subject to any disclaimer, the term of this patent is extended or adjusted under 35 U.S.C. 154(b) by 0 days.

(21) Appl. No.: 10/414,917

(22) Filed: Apr. 15, 2003

(65) Prior Publication Data
US 2004/0035180 A1 Feb. 26, 2004

(30) Foreign Application Priority Data

Apr. 18, 2002 (JP) ........................................ 2002-116288
May 22, 2002 (JP) ........................................ 2002-147419

(51) Int. Cl.⁷ ................................................ G01F 1/00
(52) U.S. Cl. ............................ 702/38; 702/45; 702/50; 702/100; 73/861
(58) Field of Search ............................ 702/38, 45, 50, 702/100; 73/861.12, 861.16, 861.17, 861.08, 861.04, 700, 735, 1.16, 861, 8

(56) References Cited

U.S. PATENT DOCUMENTS

| | | | | |
|---|---|---|---|---|
| 4,290,313 A | * | 9/1981 | Appel et al. | 73/861.17 |
| 4,303,980 A | * | 12/1981 | Yard | 702/49 |
| 4,644,799 A | * | 2/1987 | Tomita | 73/861.12 |
| 4,658,653 A | * | 4/1987 | Tomita | 73/861.12 |
| 5,388,465 A | * | 2/1995 | Okaniwa et al. | 73/861.17 |
| 5,443,552 A | * | 8/1995 | Tomita | 73/861.17 |
| 5,621,177 A | * | 4/1997 | Torimaru | 73/861.16 |

FOREIGN PATENT DOCUMENTS

| | | |
|---|---|---|
| JP | 10-111157 A | 4/1998 |
| JP | 2000-258211 A | 9/2000 |

* cited by examiner

*Primary Examiner*—John Barlow
*Assistant Examiner*—Hien Vo
(74) *Attorney, Agent, or Firm*—Blakely Sokoloff Taylor & Zafman

(57) ABSTRACT

An electromagnetic flowmeter includes a coil, exciting section, noise eliminating section, and arithmetic processing section. The coil applies a magnetic field to a fluid flowing in a pipe line. The exciting section supplies an exciting current to the coil. The noise eliminating section eliminates noise from a measurement signal detected from the fluid under excitation by using a differential frequency component between a commercial power frequency and an exciting frequency. The arithmetic processing section calculates a measurement flow rate on the basis of the measurement signal output from the noise eliminating section.

7 Claims, 12 Drawing Sheets

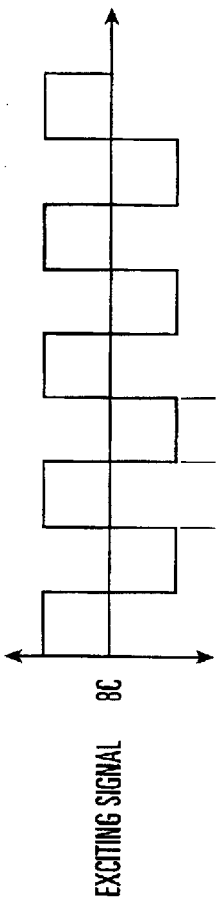
FIG. 6A EXCITING SIGNAL 8C
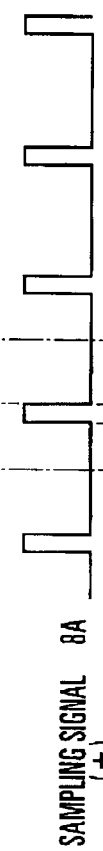
FIG. 6B SAMPLING SIGNAL (+) 8A
FIG. 6C SAMPLING SIGNAL (−) 8B
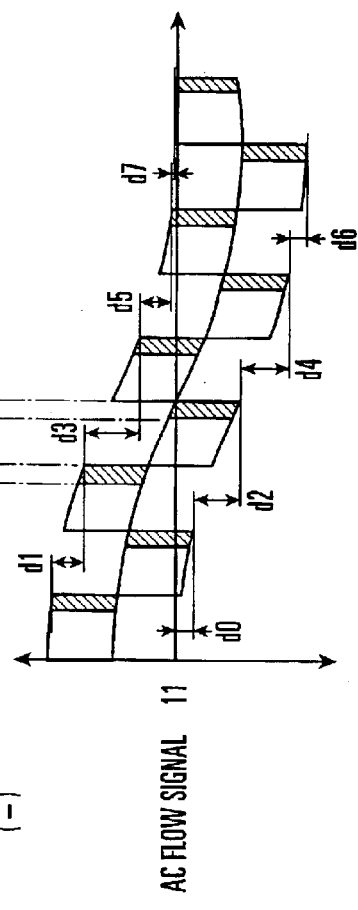
FIG. 6D AC FLOW SIGNAL 11
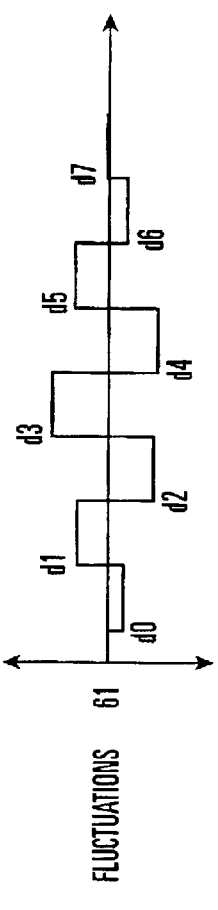
FIG. 6E FLUCTUATIONS 61

ELECTROMAGNETIC FLOWMETER

BACKGROUND OF THE INVENTION

The present invention relates to an electromagnetic flowmeter and, more particularly, to an electromagnetic flowmeter having a function of suppressing fluctuations in measurement flow rate due to commercial power noise mixed in a fluid.

When a fluid to be measured by an electromagnetic flowmeter passes through a pump or electromagnetic valve, 50-Hz/60-Hz commercial power noise caused by such a device may be mixed in the fluid. If such commercial power noise is mixed in the fluid, since the commercial power noise is superimposed on the signal electromotive force obtained from the detector, differential noise having a differential frequency between the commercial power frequency and a sampling frequency is also superimposed on the DC flow rate signal obtained by sampling the signal electromotive force. When such a DC flow rate signal is loaded as a digital flow rate signal, fluctuations occur in a measurement flow rate due to the influences of the differential noise.

Conventionally, as an electromagnetic flowmeter designed to suppress fluctuations in measurement flow rate which are caused by such commercial power noise, an electromagnetic flowmeter having a band elimination filter (to be referred to as a BEF hereinafter) 120 for eliminating differential noise in a DC flow rate signal 112A as shown in FIG. 12 has been proposed (e.g., Japanese Patent Laid-Open No. 2000-258211).

Referring to FIG. 12, a detector 100 applies a magnetic field to a fluid in a pipe line on the basis of a predetermined AC exciting current, and detects/outputs the signal electromotive force generated in a fluid as a detection signal. A converter 110 outputs a predetermined AC exciting current to the detector 100, and calculates/outputs a flow rate in the pipe line by performing signal processing for the detection signal from the detector 100.

As shown in FIGS. 13A to 13E, an exciting section 116 outputs an AC exciting current which has a predetermined frequency and is formed from a rectangular wave on the basis of an exciting signal 117C from a switching section 117.

A coil 100c of the detector 100 is excited by the AC exciting current from the converter 110 to apply a predetermined magnetic field to a fluid flowing in a pipe line 101. This generates a signal electromotive force having an amplitude corresponding to the flow velocity of the fluid.

This signal electromotive force is detected by electrodes 100a and 100b disposed on the inner wall of the pipe line 101 at positions to oppose each other, and is output as a detection signal to the converter 110.

In the converter 110, a first-stage amplification section 111 attenuates the low-frequency components of the detection signal obtained from the detector 100 by using a high-pass filter or the like so as to attenuate pulse-like noise and low-frequency noise mixed in this detection signal, AC-amplifies the signal, and outputs the resultant signal as an AC flow rate signal 111A.

A sample/hold section 112 samples each waveform trailing edge portion (hatched portion) of the AC flow rate signal 111A from the first-stage amplification section 111, which portion is affected little by the magnetic flux differential noise produced by the exciting coil 100c, and outputs the resultant signal as the DC flow rate signal 112A. The band elimination filter 120 attenuates a differential noise component with a frequency $$\Delta f = |fn - fex|$$

which corresponds to the difference between an exciting frequency fex and a commercial power frequency fn contained in the DC flow rate signal 112A from the sample/hold section 112.

An arithmetic processing section 114 loads the DC flow rate signal 112A output from the sample/hold section 112 through the BEF 120 as a digital flow rate signal, and calculates a measurement flow rate by executing predetermined arithmetic processing. An output section 115 then converts the flow rate into a predetermined flow rate signal (loop current) and outputs it.

In this manner, a measurement flow rate in which fluctuations caused by differential noise is suppressed is obtained.

An electromagnetic flowmeter is also available, which obtains an output voltage $E_S$ indicating the difference between electrode voltages $E_A$ and $E_B$ obtained from the respective detection electrodes 100a and 100b so as to reduce commercial power noise that causes differential noise instead of directly reducing the differential noise in the above manner, as shown in FIG. 14.

In general, commercial power noise mixed in a fluid tends to be equally mixed as common mode noise Nc in the respective detection electrodes 100a and 100b. When such common mode noise Nc is mixed in the fluid, the electrode voltages $E_A$ and $E_B$ generated between the respective detection electrodes 100a and 100b and ground potential 100d are given by $$E_A = S_A + N_C$$

$$E_B = S_B + N_C$$

where $S_A$ and $S_B$ are the signal electromotive forces generated by the detection electrodes 100a and 100b.

At this time, since the signal electromotive forces are expressed by $$S_A = -S_B$$

when the difference between these electrode voltages $E_A$ and $E_B$ is calculated by a subtracter 151, the output voltage $E_S$ with the common mode noise Nc being canceled is obtained:

$$E_S = E_A - E_B = 2S_A$$

In contrast to this, when the electrode voltages $E_A$ and $E_B$ are added by an adder 152, flow rate signals cancel each other, a noise voltage $E_N$ representing commercial power noise is obtained:

$$E_N = E_A + E_B = 2N_C$$

By extracting a commercial power frequency from this noise voltage and performing excitation in synchronism with the extracted frequency, the arithmetic processing section 114 can perform arithmetic operation in the subtracter 151.

More specifically, like the sample/hold section 112 shown in FIG. 12, the arithmetic processing section 114 samples the electrode voltages $E_A$ and $E_B$ in half cycles to obtain $E_S$ by using $E_A$ and $E_B$ which are phase-shifted half cycle. In this case, since the excitation timing is synchronous with the commercial power frequency, the common mode noise Nc is equally mixed in $E_A$ and $E_B$ which are phase-shifted half cycle. This eliminates the phase shift and can effectively cancel out the common mode noise Nc without using the subtracter 151.

In this manner, a measurement flow rate in which fluctuations caused by differential noise are suppressed is obtained.

Such a conventional electromagnetic flowmeter, however, additionally requires an analog signal processing circuit for suppressing fluctuations caused by differential noise having the differential frequency between a commercial power frequency and a sampling frequency. This leads to an increase in manufacturing cost and an increase in power consumption. In a two-wire electromagnetic flowmeter in which the maximum current consumption is limited to 4 mA or less, in particular, an increase in power consumption poses a serious problem.

As in the former case, when differential noise is to be eliminated by a BEF, a relatively narrow frequency band near the differential frequency must be effectively eliminated. In this case, a filter circuit with a certain scale is required, and an increase in power consumption is inevitable.

As in the latter case, when commercial power noise as a noise source is to be attenuated, the electromagnetic flowmeter requires a subtraction circuit for accurately eliminating commercial power noise from electrode voltage in opposite phases, and an addition circuit for accurately extracting a commercial power frequency from commercial power noise, resulting in an increase in current consumption.

SUMMARY OF THE INVENTION

It is an object of the present invention to provide an electromagnetic flowmeter which can realize flow rate measurement with precision increased to such an extent that no problem arises in terms of the influences of fluctuations and slurry noise caused by commercial power frequencies.

In order to achieve the above object, according to the present invention, there is provided an electromagnetic flowmeter comprising a coil which applies a magnetic field to a fluid flowing in a pipe line, exciting means for supplying an exciting current to the coil, noise eliminating means for eliminating noise from a measurement signal detected from the fluid under excitation by using a differential frequency component between a commercial power frequency and an exciting frequency, and arithmetic processing means for calculating a measurement flow rate on the basis of the measurement signal output from the noise eliminating means.

BRIEF DESCRIPTION OF THE DRAWINGS

FIGS. 6A to 6E are timing charts showing sampling operation;

DESCRIPTION OF THE PREFERRED EMBODIMENTS

An embodiment of the present invention will be described next with reference to the accompanying drawings.

Figure 1:
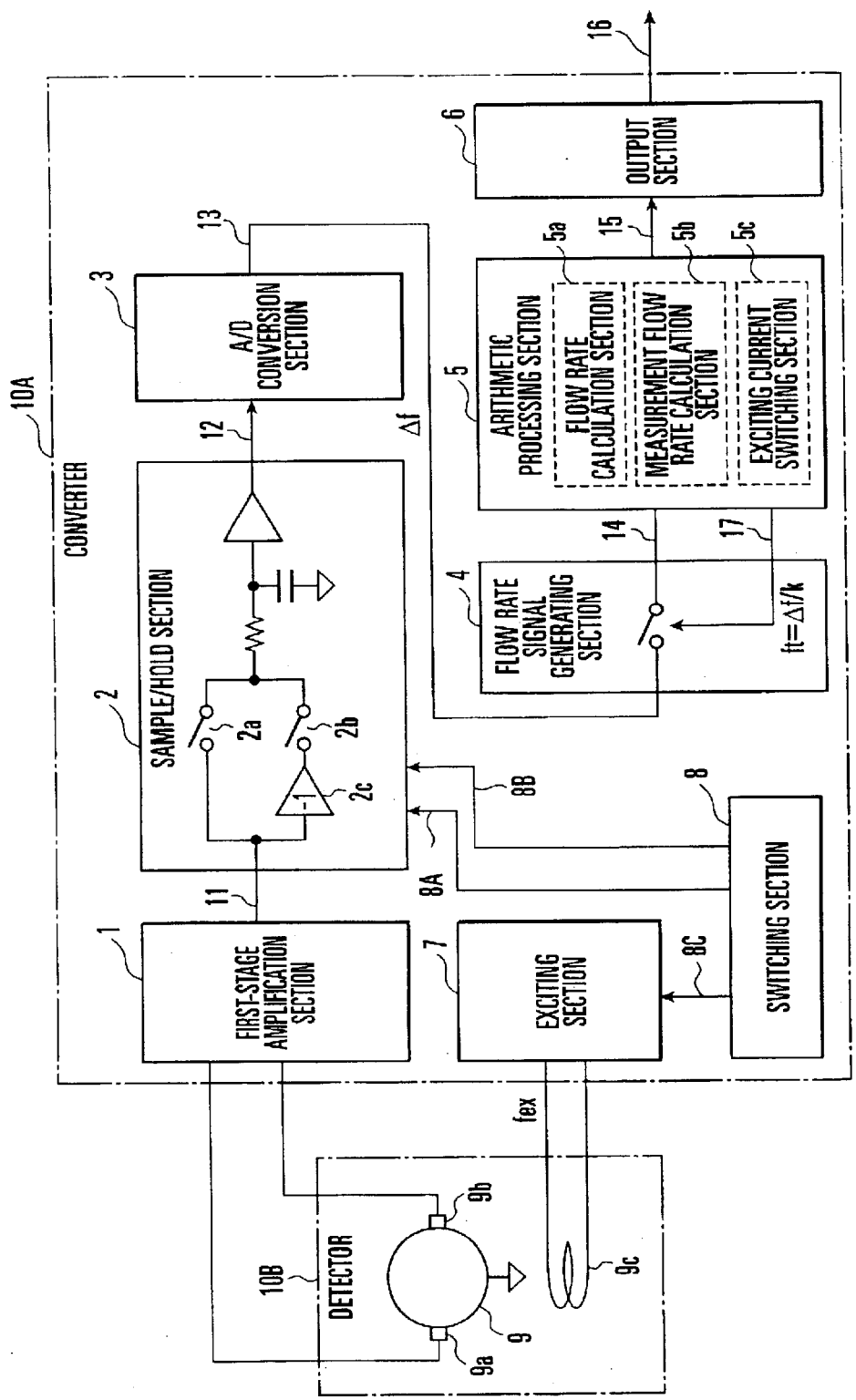
FIG. 1 is a block diagram showing the arrangement of an electromagnetic flowmeter according to the first embodiment of the present invention.

FIG. 1 shows the arrangement of an electromagnetic flowmeter according to an embodiment of the present invention. In this electromagnetic flowmeter, a detector 10B applies a magnetic field to a fluid in a pipe line on the basis of a predetermined exciting current, and detects/outputs the signal electromotive force produced in the fluid as a detection signal. A converter 10A outputs a predetermined AC exciting current to the detector 10B and calculates/outputs a flow rate in a pipe line 9 by performing signal processing of the detection signal from the detector 10B.

In the detector 10B, detection electrodes 9a and 9b are electrodes which are disposed to face the inner wall of the pipe line 9 through which a target fluid flows, and detect the signal electromotive force produced in the fluid. An exciting coil 9c is excited on the basis of an exciting current from the converter 10A and applies a magnetic field to the fluid in the pipe line 9.

In the converter 10A, a switching section 8 generates and outputs sampling signals 8A and 8B and exciting signal 8C on the basis of a predetermined clock. On the basis of the exciting signal 8C from the switching section 8, an exciting section 7 outputs an exciting current having an AC rectangular wave and predetermined frequency.

A first-stage amplifier 1 attenuates the pulse-like noise and low-frequency noise mixed in the detection signal obtained from the detection electrodes 9a and 9b of the detector 10B by using a high-pass filter, AC-amplifies the detection signal by using an AC amplification circuit, and outputs the resultant signal as an AC flow rate signal 11 whose amplitude changes with a flow rate.

A sample/hold section 2 samples the AC flow rate signal 11 from the first-stage amplifier 1 on the basis of the sampling signals 8A and 8B from the switching section 8, and outputs the resultant signal as a DC flow rate signal 12 whose DC potential changes with flow rate.

An A/D conversion section 3 A/D-converts the DC flow rate signal 12 from the sample/hold section 2 into a digital flow rate signal 13, and outputs it.

A flow rate signal generating section 4 loads the digital flow rate signal 13 from the A/D conversion section 3 at a frequency ft as a flow rate signal 14 into an arithmetic processing section 5 on the basis of a control signal 17 from the arithmetic processing section 5.

The arithmetic processing section 5 includes a flow rate calculation section 5a, measurement flow rate calculation section 5b, and exciting current switching section 5c. The flow rate calculation section 5a calculates a flow rate by executing predetermined arithmetic processing for the flow rate signal 14 input from the flow rate signal generating section 4. The measurement flow rate calculation section 5b corrects the calculated flow rate on the basis of an adjustment coefficient corresponding to the exciting current value used at that time, and outputs the resultant data as a measurement flow rate 15. The exciting current switching section 5c performs switching control on the current value of an exciting current of an exciting current on the basis of the calculated measurement flow rate.

The output section 6 converts the measurement flow rate 15 output from the arithmetic processing section 5 into a predetermined flow rate signal (loop current) 16 and outputs it.

The operation of the electromagnetic flowmeter according to the first embodiment will be described next with reference to FIGS. 2A to 2F. FIGS. 2A to 2F show the operation of the electromagnetic flowmeter according to the first embodiment.

An AC exciting current in the form of a rectangular wave with a predetermined frequency fex higher than a commercial power frequency fn is supplied from the exciting section 7 of the converter 10A to the exciting coil 9c of the detector 10B on the basis of the exciting signal 8C from the switching section 8.

The exciting coil 9c is excited by this signal to apply a predetermined magnetic field to a fluid flowing in the pipe line 9, thus generating a signal electromotive force having an amplitude corresponding to the flow velocity of the fluid.

This signal electromotive force is detected by the detection electrodes 9a and 9b disposed on the inner wall of the pipe line 9 at positions to oppose each other, and is output as a detection signal to the converter 10A. A first-stage amplification section 1 of the converter 10A attenuates the low-frequency components of the detection signal obtained from the detector 10B. The pulse-like noise and low-frequency noise mixed in the detection signal are then attenuated, and the signal is AC-amplified. The resultant signal is output as the AC flow rate signal 11.

The sample/hold section 2 samples the AC flow rate signal 11 from the first-stage amplification section 1 on the basis of the sampling period indicated by the sampling signals 8A and 8B from the switching section 8, and outputs the resultant signal as the DC flow rate signal 12.

Note that a sampling period is set in a trailing edge portion (hatched portion) of the waveform of the AC flow rate signal 11 from the first-stage amplification section 1, which is affected little by the magnetic flux differential noise produced by the exciting coil 9C. The sample/hold section 2 integrates the AC flow rate signal 11 by short-circuiting switches 2a and 2b only during this sampling period, and outputs the resultant signal as the DC flow rate signal 12.

When the AC flow rate signal 11 is on the positive side, only the switch 2a is short-circuited on the basis of the switching signal 8A. When the AC flow rate signal 11 is on the negative side, the AC flow rate signal 11 is inverted by an inverter 2c, and then only the switch 2B is short-circuited on the basis of the switching signal 8B.

The noise characteristics of the DC flow rate signal 12 output from the sample/hold section 2 will be described below.

As described above, when commercial power noise is mixed in the AC flow rate signal 11, differential noise is produced in the DC flow rate signal 12 owing to the sampling frequency in the sample/hold section 2, i.e., the exciting frequency. As a result, fluctuations occur in the measurement flow rate.

Figure 3:
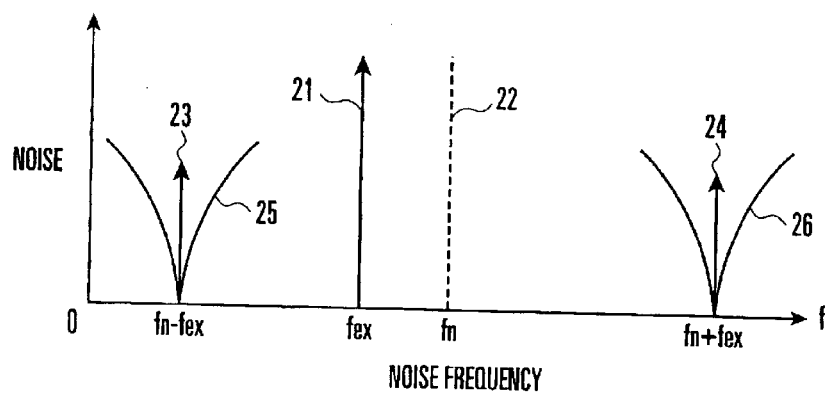
FIG. 3 is a graph for explaining the frequency characteristics of differential noise.

FIG. 3 shows the frequency characteristics of differential noise contained in a DC flow rate signal. Fluctuations occur in the DC flow rate signal 12 at the following frequency which corresponds to the difference between a frequency m times the predetermined frequency fex (21) and a frequency n times the commercial power frequency fn (22) (m and n are positive integers):

$$\Delta f = |mfex \pm nfn|$$

With m=1 and n=1, in particular, fex−fn(23) and fex+fn(24) are close to the exciting frequency fex, and hence have relatively large influences on a measurement flow rate.

Figure 2:
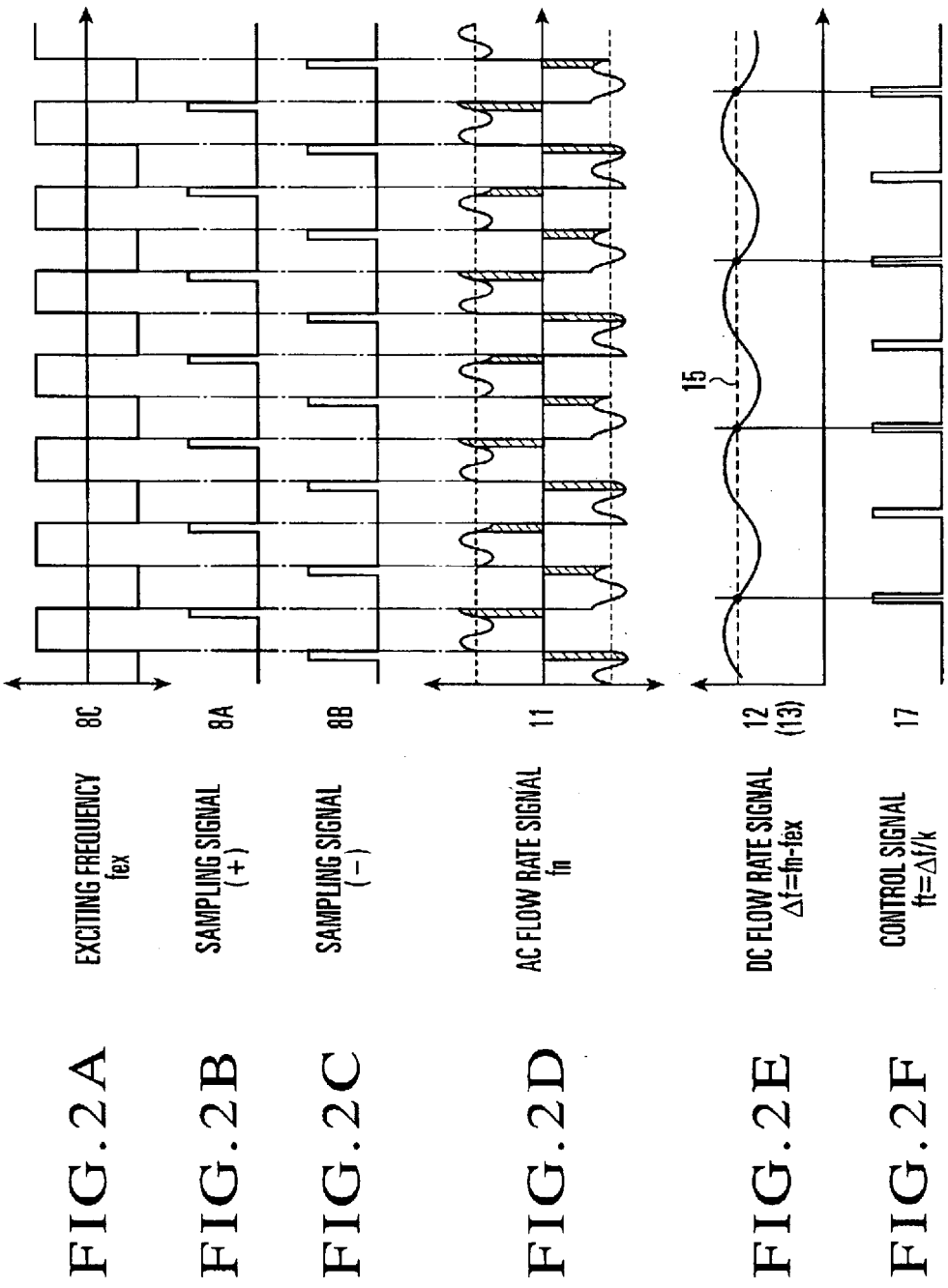
FIGS. 2A to 2F are signal waveform diagrams showing the operation of the electromagnetic flowmeter in FIG. 1.

The first embodiment includes the flow rate signal generating section 4 to load a DC flow rate signal at a predetermined timing. This suppresses fluctuations caused by the differential noise contained in a DC flow rate signal. For example, as shown in FIG. 2F, when the DC flow rate signal 12 is loaded in synchronism with the frequency of differential noise, the amounts of differential noise at the respective loading timings become almost equal to each other, thus suppressing fluctuations.

The frequency ft of this loading timing may be an integer submultiple of the frequency of differential noise, i.e., a differential frequency $\Delta f$ and given by $$ft = \Delta f / k \text{ (where } k \text{ is a natural number)}$$

Note that a differential noise component 24 is located at a frequency farther from signal frequency components (DC component and its neighboring component) than a differential noise component 23, and hence can be sufficiently attenuated by a general low-pass filter in many cases.

Since the differential noise component 24 is higher in frequency than the exciting frequency fex and is attenuated to a certain extent by averaging in the arithmetic processing section 5, the flow rate signal generating section 4 may attenuate only the differential noise component 23.

In this manner, the DC flow rate signal 12, the digital flow rate signal 13 from the A/D conversion section 3 in this case, is loaded by the flow rate signal generating section 4 at the predetermined frequency ft, and output as the flow rate signal 14 to the arithmetic processing section 5.

The arithmetic processing section 5 calculates a measurement flow rate value from the flow velocity of the fluid by executing predetermined arithmetic processing for the flow rate signal 14. The output section 6 then converts this value into a predetermined signal and outputs it.

Figure 4:
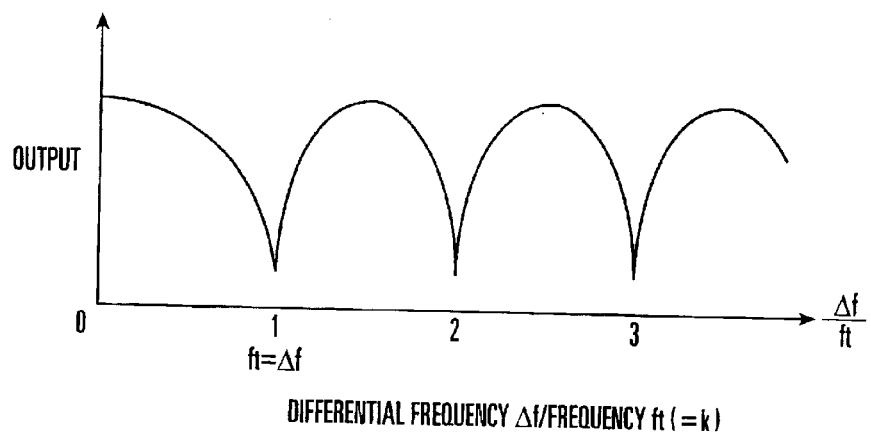
FIG. 4 is a graph for explaining the frequency characteristics of flow rate signal generation processing.

FIG. 4 explains the frequency characteristics of loading processing by the flow rate signal generating section 4. Referring to FIG. 4, the abscissa indicates the value obtained by dividing the differential frequency $\Delta f$ of differential noise by the frequency ft:

$$\Delta f / ft \ (= k)$$

and the ordinate indicates the output level.

The above processing has a characteristic that the output level greatly decreases at a frequency where $\Delta f/ft$ becomes an integer.

The relationship between the commercial power frequency and the exciting frequency (sampling frequency) or frequency ft is adjusted by using this characteristic so as to match the frequencies greatly attenuated by this processing with the differential noise components 23 and 24 (see FIG. 3), which are frequency components that cause fluctuations. This makes it possible to attenuate the fluctuations contained in the DC flow rate signal 12.

If, for example, exciting frequency fex=27.5 Hz and commercial power frequency fn=50 Hz, the frequency of differential noise on the low-frequency side becomes $\Delta f$ (=fn−fen)=2.5 Hz (m=1, n=1).

If, therefore, for example, frequency ft (=$\Delta f/k$) is 2.5 Hz, ft becomes a frequency 1/9 times (k=9) $\Delta f$. Obviously, this differential noise is suppressed. In this case, the frequency of differential noise on the high-frequency side, i.e., $$\Delta f = fn + fex$$

becomes $\Delta f$=77.5 Hz (m=1, n=1). However, since this frequency becomes 1/31 (k=31) of the differential frequency $\Delta f$, it is obvious that this differential noise is also suppressed. The differential noise can be efficiently suppressed by using submultiple frequencies of these two differential frequencies.

The frequency ft of the control signal 17 for controlling the flow rate signal generating section 4 can be easily calculated because the commercial power frequency fn and a frequency twice a sampling frequency, i.e., an exciting frequency, are known. The arithmetic processing section 5 can generate the control signal 17 having the frequency ft. Note that the generation of the control signal 17 is not limited to the arithmetic processing section 5. This signal may be generated by another circuit section, e.g., the switching section 8.

The flow rate signal generating section 4 can be implemented by a general switch circuit or gate circuit, and requires no analog signal processing circuit as in the prior art. Therefore, fluctuations caused by differential noise having the differential frequency between the commercial power frequency and the sampling frequency can be efficiently suppressed by a relatively simple circuit arrangement without much increasing the power consumption.

Note that the flow rate signal generating section 4 may be implemented by a loading timing control function based on the input port of the CPU of the arithmetic processing section 5, or selection processing of the digital flow rate signal 13 inside the arithmetic processing section 5. Alternatively, this function may be implemented by supplying the control signal 17 to the A/D conversion section 3 and using the conversion timing control function of A/D conversion processing in the A/D conversion section 3.

The above description has exemplified the scheme of transmitting a signal and power sharing the same pair of signal lines, i.e., the two-wire electromagnetic flowmeter. However, the present invention is not limited to this. The present invention can also be applied to a scheme of transmitting a signal and power through different lines, e.g., a four-wire electromagnetic flowmeter, to obtain the same effects as those described above.

An electromagnetic flowmeter according to the second embodiment will be described next.

The electromagnetic flowmeter according to the second embodiment can operate on both 50-Hz commercial power and 60-Hz commercial power.

Figure 5:
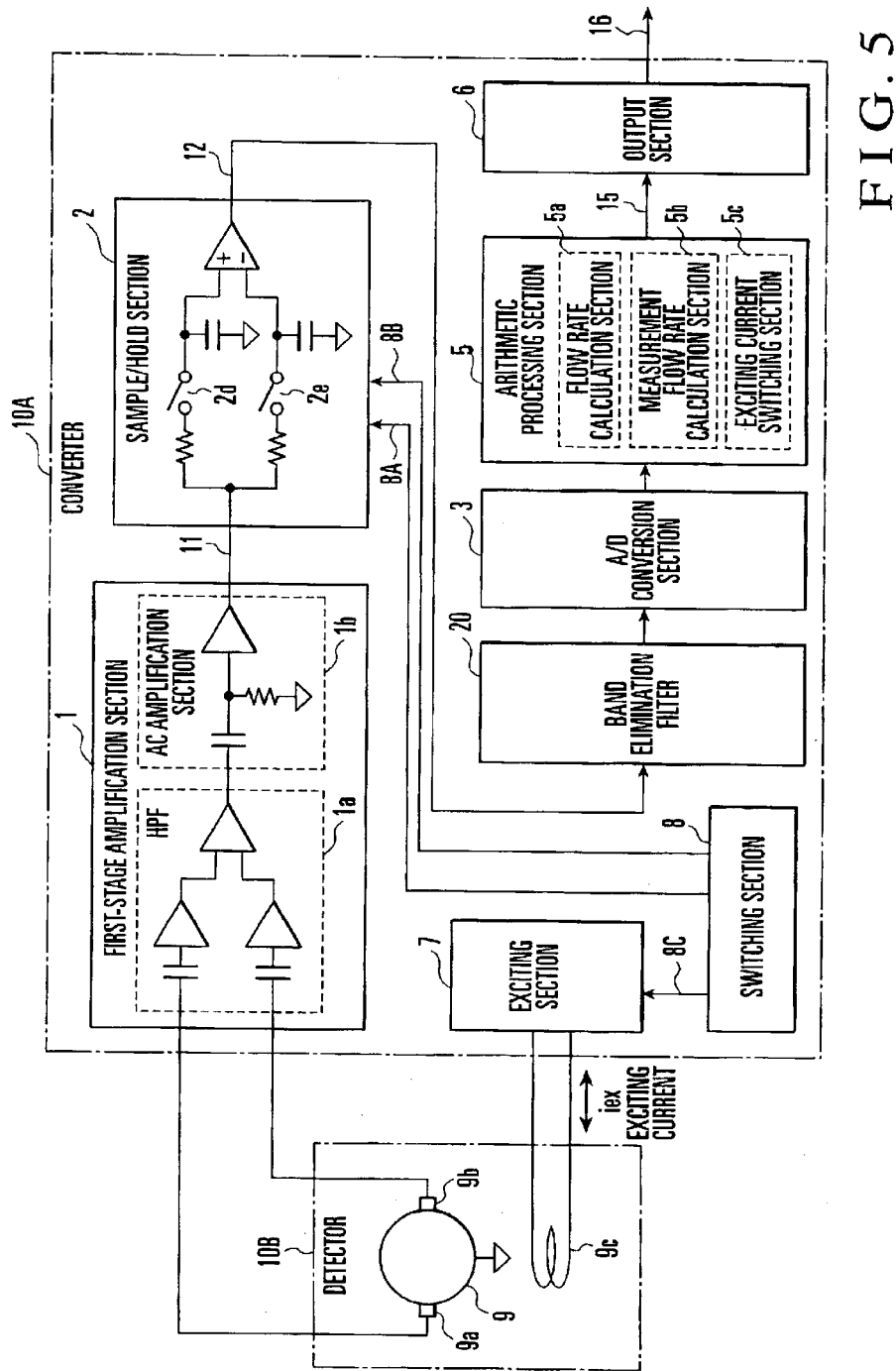
FIG. 5 is a block diagram showing an electromagnetic flowmeter according to the second embodiment of the present invention.

FIG. 5 shows the electromagnetic flowmeter according to the second embodiment. The same reference numerals as in FIG. 5 denote the same or equivalent parts of the electromagnetic flowmeter (see FIG. 1) according to the first embodiment.

Referring to FIG. 5, a detector 10B applies an AC magnetic field to a fluid in a pipe line on the basis of a predetermined exciting current, and detects/outputs the signal electromotive force produced in the fluid as a detection signal. A converter 10A outputs a predetermined AC exciting current to the detector 10B and calculates/outputs a flow rate in a pipe line by performing signal processing of the detection signal from the detector 10B.

In the detector 10B, detection electrodes 9a and 9b are electrodes which are disposed to face the inner wall of the pipe line 9 through which a target fluid flows, and detect the signal electromotive force produced in the fluid. An exciting coil 9c is excited on the basis of an AC exciting current from the converter 10A and applies a magnetic field to the fluid in the pipe line 9.

In the converter 10A, a switching section 8 generates and outputs sampling signals 8A and 8B and exciting signal 8C on the basis of a predetermined clock. On the basis of the exciting signal 8C from the switching section 8, an exciting section 7 outputs an AC exciting current having an AC rectangular wave and predetermined frequency.

A first-stage amplification section 1 includes a high-pass filter (to be referred to as an HPF hereinafter) 1a and an AC amplification section 1b. The HPF 1a attenuates the low-frequency components of the detection signal obtained from the detection electrodes 9a and 9b of the detector 10B to attenuate the pulse-like noise and low-frequency noise mixed in the detection signal. The AC amplification section 1b AC-amplifies the detection signal from the HPF 1a and outputs the resultant signal as an AC flow rate signal 11 whose amplitude changes with the flow velocity of the fluid. A sample/hold section 2 samples the AC flow rate signal 11 from the first-stage amplifier 1 on the basis of the sampling signals 8A and 8B from the switching section 8, and outputs the resultant signal as a DC flow rate signal 12 whose DC potential changes with the flow velocity of the fluid.

A band elimination filter (to be referred to a BEF hereinafter) 20 attenuates a frequency component corresponding to the difference between the exciting frequency and the commercial power frequency which is contained in the DC flow rate signal 12 from the sample/hold section 2. An A/D conversion section 3 converts the DC flow rate signal 12 from the BEF 20 into digital information by integrating it.

An arithmetic processing section 5 includes a flow rate calculation section 5a, measurement flow rate calculation section 5b, and exciting current switching section 5c. The measurement flow rate calculation section 5b calculates a flow rate by executing predetermined arithmetic processing for the digital information from the A/D conversion section 3. The measurement flow rate calculation section 5b corrects the calculated flow rate on the basis of an adjustment coefficient corresponding to an exciting current value at that time, and outputs the resultant data as a measurement flow rate 15. The exciting current switching section 5c performs switching control on the current value of an exciting current on the basis of the calculated measurement flow rate.

An output section 6 converts the measurement flow rate calculated by the arithmetic processing section 5 into a predetermined signal, and outputs it.

The operation of the electromagnetic flowmeter according to the second embodiment will be described next.

FIGS. 6A to 6E show the timing of sampling operation. Referring to FIGS. 6A to 6E, reference numeral 8C denotes the exciting signal from the switching section 8; 11, the AC flow rate signal (see FIG. 5) input to the sample/hold section 2; and 8A and 8B, the sampling signals input from the switching section 8 to the sample/hold section 2, which define a sampling period (hatched portion) of the AC flow rate signal 11.

In this case, a sampling period is set near the trailing edge of each pulse of the exciting signal 8C (AC flow rate signal 11) in consideration of its waveform stability. The sample/hold section 2 short-circuits switches 2d and 2e only during this sampling period to integrate the AC flow rate signal 11, and outputs the resultant signal as the DC flow rate signal 12. When the AC flow rate signal 11 is on the positive side, only the switch 2d is short-circuited on the basis of the switching signal 8A. When the AC flow rate signal 11 is on the negative side, only the switch 2e is short-circuited on the basis of the switching signal 8B.

The exciting section 7 of the converter 10A outputs an AC exciting current in the form of a rectangular wave with a predetermined frequency fex lower than a commercial power frequency fac on the basis of the exciting signal 8C from the switching section 8, thus exciting the exciting coil 9c of the detector 10B.

With this operation, the exciting coil 9c is excited to apply a predetermined magnetic field to a fluid flowing in the pipe line 9, thereby generating a signal electromotive force having an amplitude corresponding to the flow velocity of the fluid.

This signal electromotive force is detected by the electrodes 9a and 9b disposed on the inner wall of the pipe line 9 at positions to oppose each other, and is output as a detection signal to the converter 10A.

The HPF 1a of the converter 10A attenuates the low-frequency components of the detection signal obtained from the detector 10B to attenuate the pulse-like noise and low-frequency nose mixed in the detection signal.

Subsequently, the AC amplification section 1b AC-amplifies the output from the HPF 1a and outputs the resultant signal as the AC flow rate signal 11.

The sample/hold section 2 samples the AC flow rate signal 11 from the AC amplification section 1b on the basis of the sampling period (see FIGS. 6B and 6C) indicated by the switching signals 8A and 8B from the switching section 8, and outputs the resultant signal as the DC flow rate signal 12.

Note that a sampling period is set near the trailing edge of each pulse of the AC flow rate signal 11 in consideration of its waveform stability. The sample/hold section 2 short-circuits the switches 2d and 2e only during this sampling period to integrate the AC flow rate signal 11, and outputs the resultant signal as the DC flow rate signal 12.

When the AC flow rate signal 11 is on the positive side, only the switch 2d is short-circuited on the basis of the switching signal 8A. When the AC flow rate signal 11 is on the negative side, only the switch 2e is short-circuited on the basis of the switching signal 8B.

The BEF 20 attenuates a frequency component of the DC flow rate signal 12 which corresponds to the difference between the exciting frequency fex and the commercial power frequency fac (50/60 Hz).

The noise characteristics of the DC flow rate signal 12 output from the sample/hold section 2 will be described below.

As described above (see FIGS. 6A to 6E), when noise with a commercial power frequency is mixed in the AC flow rate signal 11, fluctuations occur in the DC flow rate signal 12 owing to the operation characteristics of the sample/hold section 2.

Figure 7:
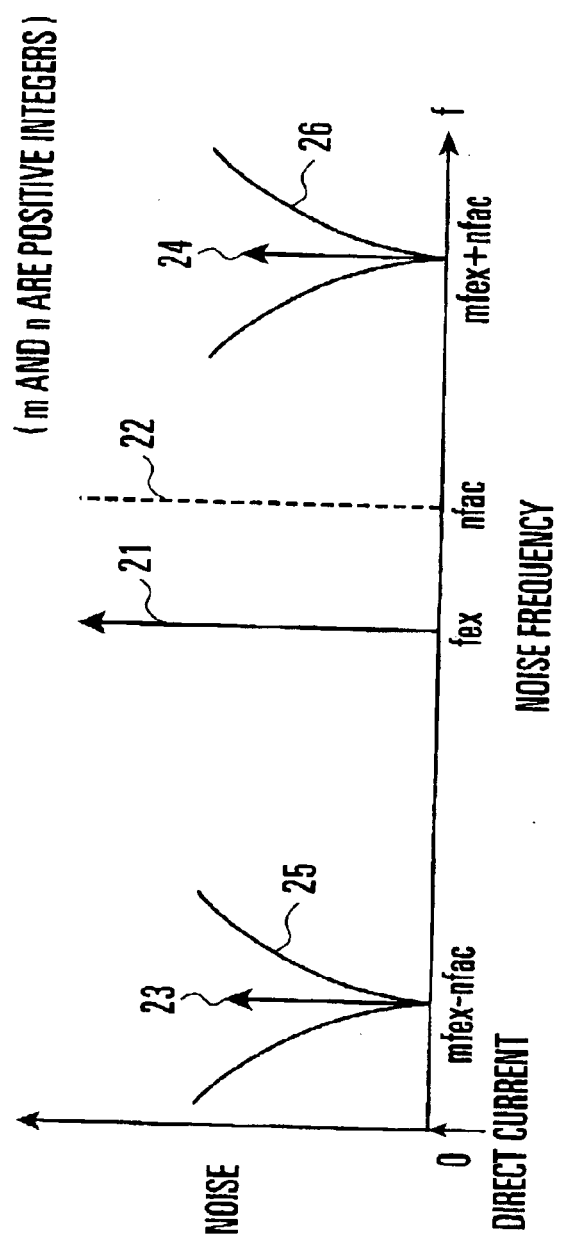
FIG. 7 is a graph for explaining the relationship between noise frequencies and fluctuations in a sample/hold section.

FIG. 7 explains the frequency characteristics of fluctuations contained in a DC flow rate signal. Fluctuations occur in the DC flow rate signal 12 at a frequency corresponding to the difference between a frequency m times the exciting frequency fex (21) and a frequency n times the commercial power frequency fac (22) (m and n are positive integers, and m or n is other than 1), i.e., mfex−nfac (23) and mfex+nfac (24).

If, therefore, the BEF 20 having frequency characteristics 25 and 26 in FIG. 7 is connected to the output stage of the sample/hold section 2 to attenuate difference frequency components 23 and 24 contained in the DC flow rate signal 12, fluctuations caused by commercial power frequency noise can be attenuated.

In the second embodiment, frequency components are attenuated by the BEF 20 in consideration of fluctuations caused by both 50-Hz commercial power noise and 60-Hz commercial power noise. More specifically, letting fex be an exciting frequency (e.g., 27.5 Hz), fac1 be the first commercial power frequency (e.g., 50 Hz), and fac2 be the second commercial power frequency (e.g., 60 Hz), the BEF 20 is used to attenuate a frequency component f that satisfies $$f=|m1fex \pm n1fac1|=|m2fex \pm 2fac2|$$

where m1, n1, m2, and n2 are positive integers.

This makes it possible to attenuate the respective fluctuations caused by the two kinds of the commercial power frequency noise.

Note that the frequency component 24 represented by mfex+nfac is located at a high frequency farther from the signal frequency component (DC component and its neighboring component) than the differential noise component 23, and hence can be sufficiently attenuated by a general LPF in many cases.

Since the frequency component 24 is higher in frequency than the exciting frequency fex and is attenuated to a certain extent by processing in the integrating A/D conversion section 3 or the arithmetic processing section 5 on the subsequent stage, the BEF 20 may attenuate only the differential noise component 23.

In this manner, the BEF 20 attenuates the fluctuations caused in the DC flow rate signal 12 by commercial frequency noise, and outputs the resultant signal to the A/D conversion section 3.

The A/D conversion section 3 outputs the DC flow rate signal 12 from the BEF 20 as digital information corresponding to its DC potential.

The arithmetic processing section 5 loads the DC flow rate signal 12 from the sample/hold section 2 as digital information through the A/D conversion section 3, and executes predetermined arithmetic processing to calculate a measurement flow rate value from the flow velocity of the fluid. An output section 6 converts this value into a predetermined signal and outputs it.

Note that the BEF 20 may have a general arrangement constituted by an active filter or digital filter. If, however, the BEF 20 is implemented by the A/D conversion section 3 using the frequency characteristics of moving averaging processing, there is no need to prepare the BEF 20 as a separate component.

Figure 8:
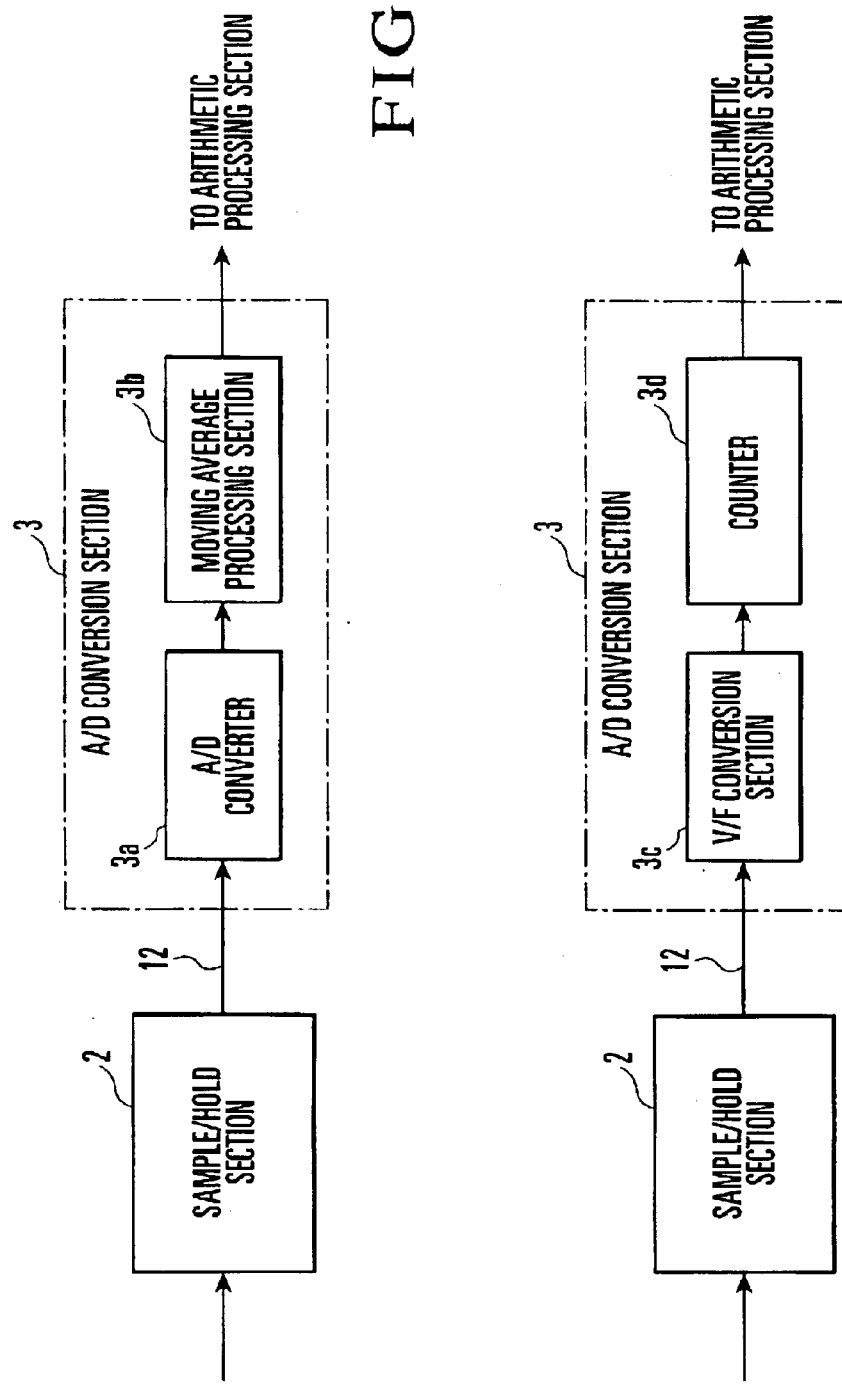
FIGS. 8A and 8B are block diagrams showing examples of the arrangement of an A/D conversion section.

FIGS. 8A and 8B explain examples of the arrangement of the A/D conversion section 3. FIG. 8A shows a case wherein a moving average processing section is used. FIG. 8B shows a case wherein a voltage/frequency conversion section is used.

Referring to FIG. 8A, an A/D converter 3a converts outputs from the BEF 20 into pieces of digital information. A moving average processing section 3b sequentially calculates the average values of a plurality of consecutive data of these pieces of digital information, and outputs them to the arithmetic processing section 5.

The DC flow rate signal 12 from the sample/hold section 2 is therefore sequentially converted into digital information by the A/D converter 3a. In addition, the moving average processing section 3b averages these pieces of digital information with pieces of consecutive digital information preceding or succeeding them. As a consequence, the pulse-like noise mixed in the original DC flow rate signal 12 is attenuated.

Figure 9:
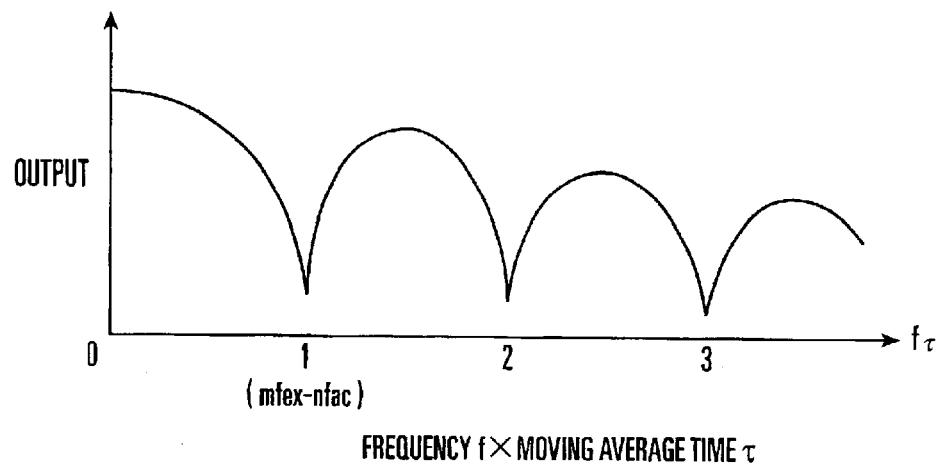
FIG. 9 is a graph for explaining the frequency characteristics of moving average processing.

FIG. 9 explains the frequency characteristics of moving average processing. The abscissa represents a product fτ of an input signal frequency f and a moving average time τ, and the ordinate, the output level.

The moving average time τ is a predetermined time interval corresponding to the number of data of sequentially input digital information which are subjected to moving average processing.

The moving average processing has a characteristic that the output level is greatly attenuated at a frequency corresponding to an integer multiple of the product fτ of the moving average time τ and the input signal frequency f.

The time interval τ in which moving average processing is performed is selected by using this characteristic, and a frequency at which the output level after moving average processing is greatly attenuated is matched with the frequency components 23 and 24 (see FIG. 7) which are the frequency components of the fluctuations described above, thereby attenuating the fluctuations contained in the DC flow rate signal 12.

If, for example, a frequency component with commercial power frequency fac1=50 Hz (n=1) is produced at exciting frequency fex=27.5 Hz (m=1), fluctuations occur at difference frequency f (=|mfex−nfac|)=22.5 Hz on the low-frequency side. By setting moving average time τ=0.0444 s, therefore, f τ=1, and frequency f=22.5 Hz can be greatly attenuated.

FIG. 8B shows a case wherein the A/D conversion section 3 is formed from a voltage/frequency conversion section 3c (to be referred to as a V/F conversion section hereinafter).

The V/F conversion section 3c integrates an input signal voltage by a predetermined time constant, and outputs a frequency pulse corresponding to the integrated voltage value. It is known that this component has a characteristic similar to that of the above moving average processing.

In this case, pulses from the V/F conversion section 3c are counted by a counter 3d at predetermined intervals, and each count value is output as digital information to the arithmetic processing section 5.

The use of the V/F conversion section 3c, therefore, decreases the cost of the circuit constituent parts, compared with the use of the A/D converter 3a and moving average processing section 3b described above, thereby achieving a reduction in the cost of the converter 10A.

Figure 10:
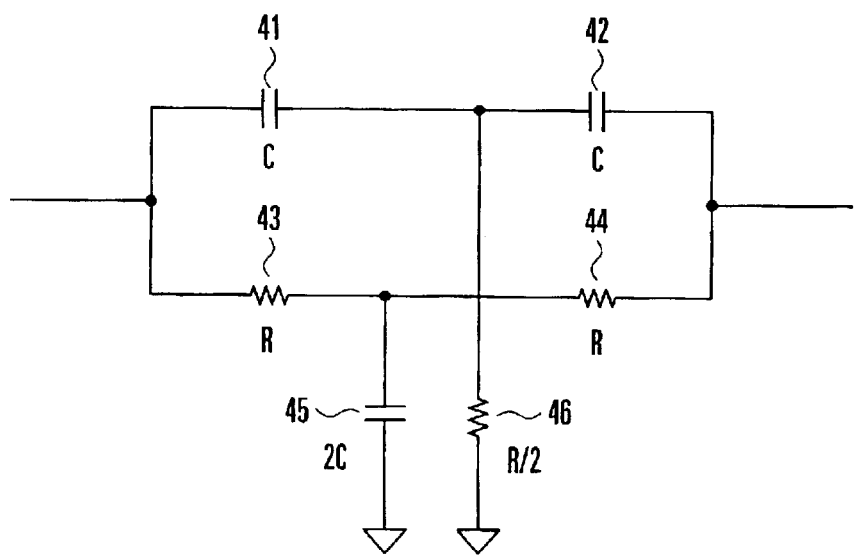
FIG. 10 is a circuit diagram showing an example of the arrangement of a BEF.

FIG. 10 shows an example of the arrangement of the BEF 20 formed from a passive filter.

FIG. 10 shows an example of the arrangement of the BEF 20. In this case, series-connected capacitive elements 41 and 42 are connected in parallel with series-connected resistive elements 43 and 44. A resistive element 45 is connected between ground potential and the node of the capacitive elements 41 and 42, and capacitive element 46 is connected between ground potential and the node of the resistive elements 43 and 44, thereby forming the BEF 20. The BEF 20 having a desired frequency characteristic can be formed by selecting values for the capacitive elements 41, 42, and 46 and resistive elements 43, 44, and 45.

There are many examples of the arrangement of the BEF other than those described above, and similar effects can be obtained by using any of them.

Figure 12:
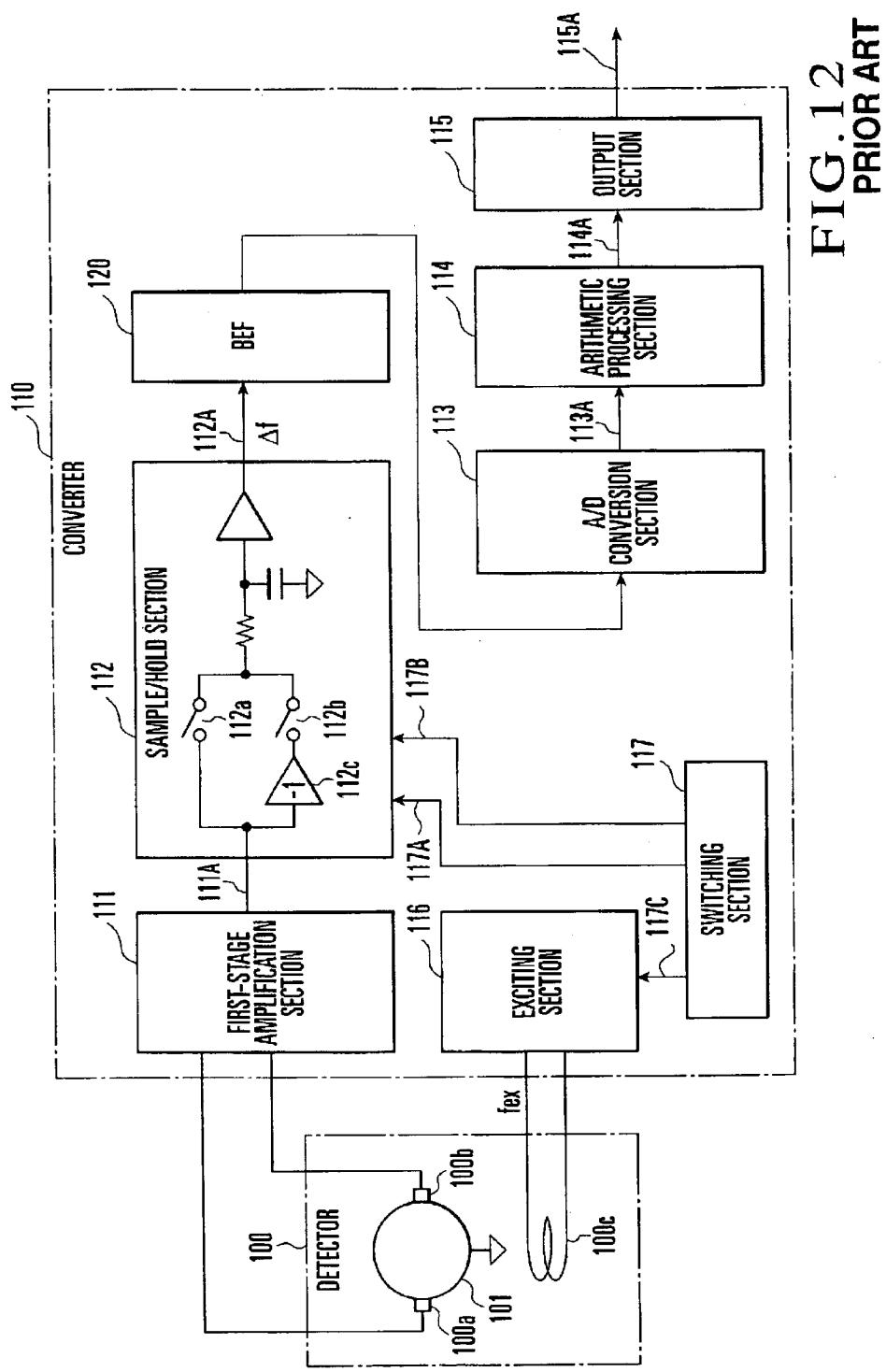
FIG. 12 is a block diagram showing the arrangement of a conventional electromagnetic flowmeter.
Figure 13:
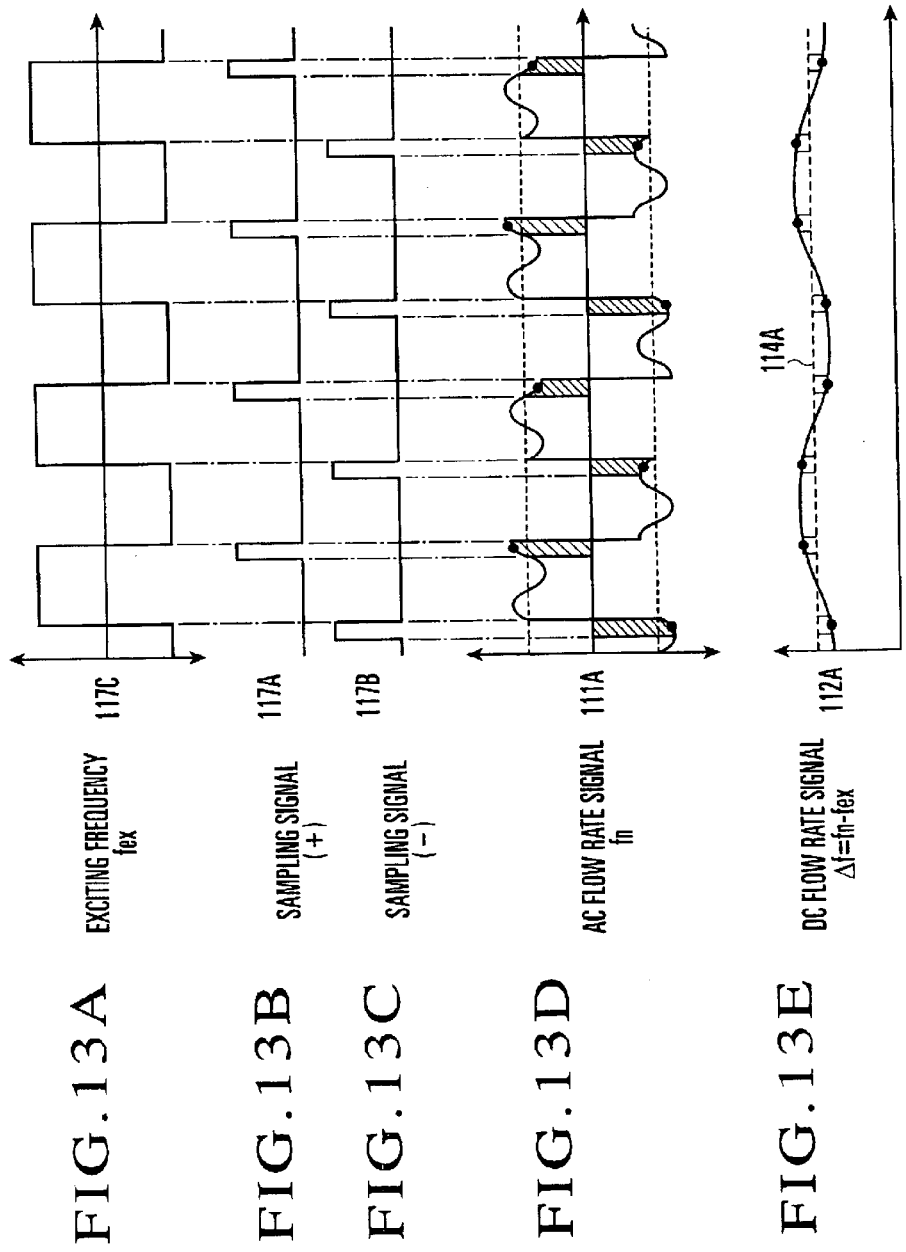
FIGS. 13A to 13E are signal waveform diagrams showing the operation of the electromagnetic flowmeter in FIG. 12.
Figure 14:
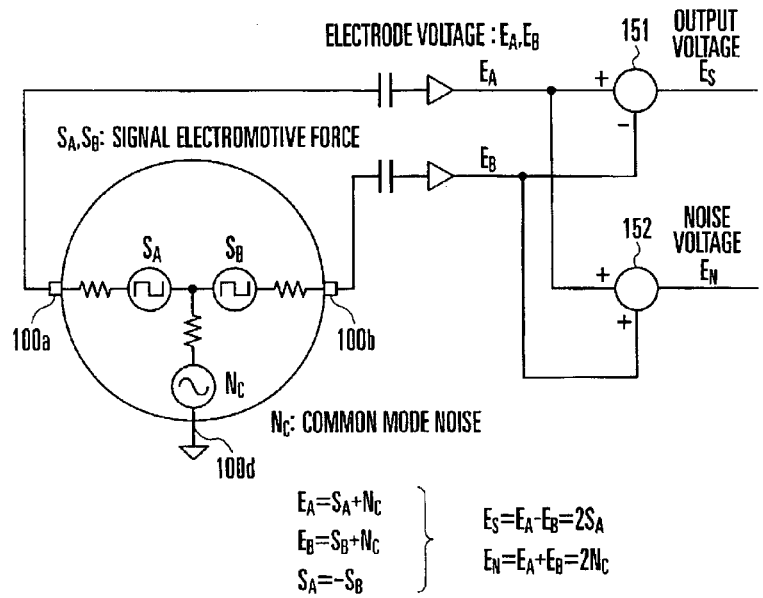
FIG. 14 is a view for explaining the basic arrangement of another conventional electromagnetic flowmeter.
Figure 15:
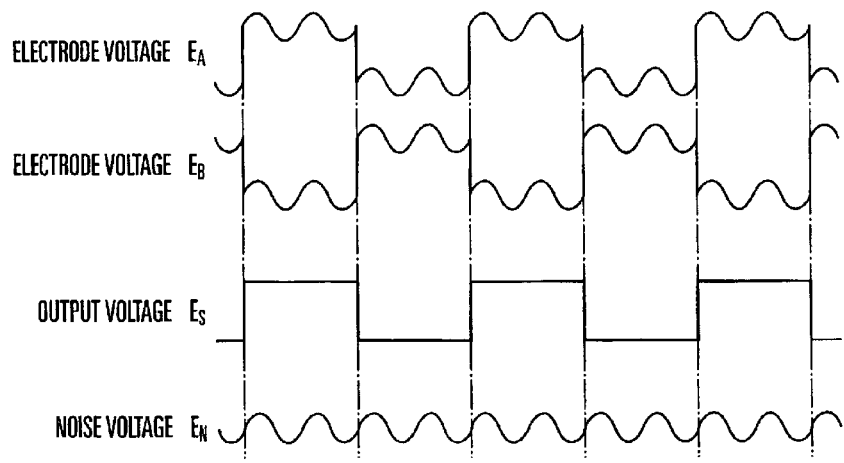
FIG. 15 is a signal waveform diagram showing the operation of the electromagnetic flowmeter in FIG. 14.

The function of the electromagnetic flowmeter according to the second embodiment will be described next. In the conventional electromagnetic flowmeter shown in FIG. 12, when continuous noise with a predetermined frequency, e.g., noise with a frequency equal to a commercial frequency of 50/60 Hz, is mixed in the AC flow rate signal 111A, fluctuations 61 occur in the DC flow rate signal 112A output from the sample/hold section 112 due to its operation characteristics. For example, as shown in FIG. 6E, when the flow rate is kept constant, noise of this type is mixed in the AC flow rate signal 111A.

In this case, errors d0 to d7 are produced in the AC flow rate signal 111A in the sampling periods of adjacent pulse waveforms due to the amplitude of the mixed noise. These errors d0 to d7 are sampled by the sample/hold section 112, and the resultant signal is output as the DC flow rate signal 112A having the fluctuations 61.

Figure 11:
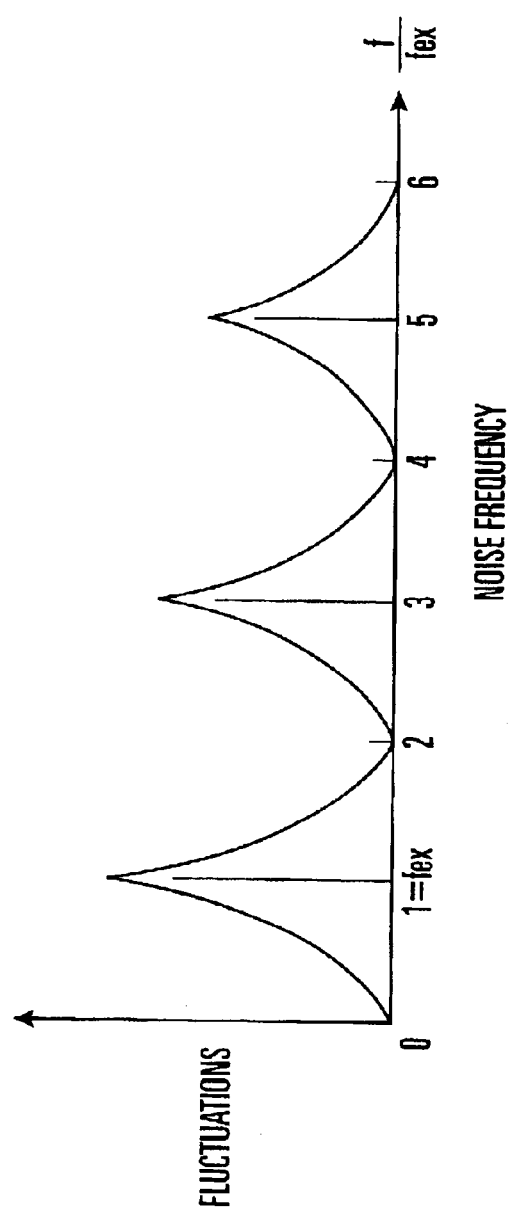
FIG. 11 is a graph for explaining the frequency characteristics of fluctuations.

FIG. 11 shows the relationship between the noise frequency and the fluctuations in the sample/hold section 112. Referring to FIG. 11, the abscissa represents the noise frequencies which are multiples of the exciting frequency; and the ordinate, the magnitudes of fluctuations.

In this case, a mountain-shaped characteristic curve appears; the magnitude of fluctuations becomes maximum when noise with a noise frequency equal to the exciting frequency fex is mixed in the signal, and the magnitude of fluctuations gradually decrease with the distance from the exciting frequency fex as the center and theoretically becomes zero at zero frequency and a noise frequency twice the exciting frequency fex. Likewise, mountain-like characteristic curves consecutively appear; the magnitude of fluctuations theoretically becomes zero at noise frequencies equal to even multiples of the exciting frequency, e.g., two times, four times, . . . which are adjacent to noise frequencies equal to odd multiples of the exciting frequency, e.g., three times, five times, . . . , each of which serves as the center.

If, therefore, a band elimination filter 120 is connected to the output stage of the sample/hold section 112, and the exciting frequency and commercial power frequency of the frequency components contained in a DC flow rate signal are respectively represented by fex and fac, a component with a frequency f given by the following equation is attenuated:

$$f = |mfex \pm nfac|$$

(where m and n are positive integers)

This arrangement suppresses the influences of harmonic components produced by the distortion of commercial power frequency noise, and reduces slurry noise produced by a slurry fluid. The arrangement also attenuates the fluctuations caused in the DC flow rate signal after sampling by commercial power frequency noise.

Such an electromagnetic flowmeter, however, is assumed to use a predetermined exciting frequency higher than a commercial power frequency, and hence requires relatively expensive exciting circuit (converter) and magnetic circuit (detector).

If the electromagnetic flowmeter uses an exciting frequency higher than a commercial power frequency, e.g., 85 Hz, a high exciting voltage is required to speed up the rise time of an exciting current in the exciting circuit because the rise time of a magnetic flux needs to be extremely sped up. At this time, after the exciting current rises up and becomes stabilized with a high voltage being kept, all the high voltage generates heat, and the converter is affected by the heat.

In order to prevent this, a circuit arrangement is required, which applies a high voltage only when an exciting current rises, and switches the voltage to a low voltage when the current is stabilized. In addition, large, expensive components having high breakdown voltage must be selected as electronic components because a high voltage is handled.

In order to speed up the rise time of a magnetic flux, a magnetic material with high magnetic response must be selected as the core of the magnetic circuit. Such a magnetic material has a high relative permeability, but has a high resistivity and becomes expensive. In a metal measurement pipe, a reduction in eddy current loss must be realized. The measurement pipe must be processed in consideration of this, resulting in high cost.

In addition, a scheme of synchronizing an exciting frequency with a commercial power frequency is conceivable. However, since there are two types of commercial power frequencies, i.e., 50 Hz and 60 Hz, band elimination filters having different cutoff frequencies are required for 50 Hz and 60 Hz. In addition, exciting circuits for outputting exciting currents with exciting frequencies corresponding to the commercial power frequencies are required. Therefore, two types of electromagnetic flowmeters having band elimination filters and exciting circuits which correspond to the commercial power frequencies may be separately manufactured for the respective commercial power frequencies, but each electromagnetic flowmeter cannot be used for both the commercial power frequencies. An arrangement may be designed such that two types of band elimination filters are prepared, and the band elimination filters and exciting frequencies corresponding to the commercial power frequencies are switched and used. In this case, however, the circuit size becomes large and the cost increases.

A scheme is conceivable in which AC noise of the two commercial powers is eliminated by selecting exciting frequencies such that the time interval between the sampling start time of the first half of an exciting period and the sampling start time of the second half becomes an integer multiple of the period of each of 50-Hz commercial power and 60-Hz commercial power (see, e.g., Japanese Patent Laid-Open No. 10-111157). In this scheme, however, since the exciting frequency must be set to an integer multiple of 200 ms, the exciting frequency becomes that for infrasonic wave excitation, e.g., 5 Hz, 2.5 Hz, or 1.67 Hz. The influences of slurry noise cannot be neglected.

In the electromagnetic flowmeter according to the second embodiment, therefore, a magnetic field is applied to a fluid in the pipe by using an AC exciting current with a frequency lower than commercial power frequencies of 50 and 60 Hz, and a measurement flow rate is obtained by performing signal processing of a signal electromotive force of the fluid which is obtained from the electrodes.

Tables 1a and 1b show frequency components of fluctuations at the respective commercial power frequencies.

TABLE 1(a)

| | | | | | | | (Hz) |
|---|---|---|---|---|---|---|---|
| | n1 | 1 | 2 | 3 | 4 | 5 | 6 | 7 |
| m1 | m1fex\n1fac1 | 50.0 | 100.0 | 150.0 | 200.0 | 250.0 | 300.0 | 350.0 |
| 1 | 27.5 | ▓▓ | 72.5 | 122.5 | 172.5 | 222.5 | 272.5 | 322.5 |
| 2 | 55.0 | 5.0 | 45.0 | 95.0 | 145.0 | 195.0 | 245.0 | 295.0 |
| 3 | 82.5 | 32.5 | ▓▓ | 67.5 | 117.5 | 167.5 | 217.5 | 267.5 |
| 4 | 110.0 | 60.0 | 10.0 | 40.0 | 90.0 | 140.0 | 190.0 | 240.0 |
| 5 | 137.5 | 87.5 | 37.5 | ▓▓ | 62.5 | 112.5 | 162.5 | 212.5 |
| 6 | 165.0 | 115.0 | 65.0 | 15.0 | 35.0 | 85.0 | 135.0 | 185.0 |
| 7 | 192.5 | 142.5 | 92.5 | 42.5 | ▓▓ | 57.5 | 107.5 | 157.5 |
| 8 | 220.0 | 170.0 | 120.0 | 70.0 | 20.0 | 30.0 | 80.0 | 130.0 |
| 9 | 247.5 | 197.5 | 147.5 | 97.5 | 47.5 | ▓▓ | 52.5 | 102.5 |
| 10 | 275.0 | 225.0 | 175.0 | 125.0 | 75.0 | 25.0 | 25.0 | 75.0 |
| 11 | 302.5 | 252.5 | 202.5 | 152.5 | 102.5 | 52.5 | ▓▓ | 47.5 |
| 12 | 330.0 | 280.0 | 230.0 | 180.0 | 130.0 | 80.0 | 30.0 | 20.0 |
| 13 | 357.5 | 307.5 | 257.5 | 207.5 | 157.5 | 107.5 | 57.5 | ▓▓ |
| 14 | 385.0 | 335.0 | 285.0 | 235.0 | 185.0 | 135.0 | 85.0 | 35.0 |
| 15 | 412.5 | 362.5 | 312.5 | 262.5 | 212.5 | 162.5 | 112.5 | 62.5 |

TABLE 1(b)

| | | | | | | | (Hz) |
|---|---|---|---|---|---|---|---|
| | n2 | 1 | 2 | 3 | 4 | 5 | 6 | 7 |
| m2 | m2fex\n2fac2 | 60.0 | 120.0 | 180.0 | 240.0 | 300.0 | 360.0 | 420.0 |
| 1 | 27.5 | 32.5 | 92.5 | 152.5 | 212.5 | 272.5 | 332.5 | 392.5 |
| 2 | 55.0 | 5.0 | 65.0 | 125.0 | 185.0 | 245.0 | 305.0 | 365.0 |
| 3 | 82.5 | ▓▓ | 37.5 | 97.5 | 157.5 | 217.5 | 277.5 | 337.5 |
| 4 | 110.0 | 50.0 | 10.0 | 70.0 | 130.0 | 190.0 | 250.0 | 310.0 |
| 5 | 137.5 | 77.5 | ▓▓ | 42.5 | 102.5 | 162.5 | 222.5 | 282.5 |
| 6 | 165.0 | 105.0 | 45.0 | 15.0 | 75.0 | 135.0 | 195.0 | 255.0 |
| 7 | 192.5 | 132.5 | 72.5 | ▓▓ | 47.5 | 107.5 | 167.5 | 227.5 |
| 8 | 220.0 | 160.0 | 100.0 | 40.0 | 20.0 | 80.0 | 140.0 | 200.0 |
| 9 | 247.5 | 187.5 | 127.5 | 67.5 | ▓▓ | 52.5 | 112.5 | 172.5 |
| 10 | 275.0 | 215.0 | 155.0 | 95.0 | 35.0 | 25.0 | 85.0 | 145.0 |
| 11 | 302.5 | 242.5 | 182.5 | 122.5 | 62.5 | ▓▓ | 57.5 | 117.5 |
| 12 | 330.0 | 270.0 | 210.0 | 150.0 | 90.0 | 30.0 | 30.0 | 90.0 |
| 13 | 357.5 | 297.5 | 237.5 | 177.5 | 117.5 | 57.5 | ▓▓ | 62.5 |
| 14 | 385.0 | 325.0 | 265.0 | 205.0 | 145.0 | 85.0 | 25.0 | 35.0 |
| 15 | 412.5 | 352.5 | 292.5 | 232.5 | 172.5 | 112.5 | 52.5 | ▓▓ |

▓▓ : frequency to be attenuated

As described above (see FIG. 11), of the fluctuations contained in the DC flow rate signal 12, fluctuations caused by the exciting frequency fex itself (m=1) exhibit the highest level, and the fluctuations caused by harmonics equivalent to odd multiples of the exciting frequency fex gradually decreases in level with the distance from fex.

Frequency components higher in frequency than the exciting frequency fex can be easily attenuated by a general LPF, and fluctuations caused by these components can be easily attenuated. Therefore, the BEF 20 may attenuate the frequency component f of the fluctuations that can be produced in a region lower than the exciting frequency fex.

Assume that exciting frequency fex=27.5 Hz. In this case, at commercial power frequency fac1=50 Hz, as indicted by Table 1(a), as the frequency component of fluctuations that can be produced in a region lower than fex, i.e., $$f=|m1fex\pm n1fac1|$$

the following fluctuations are produced by harmonics equivalent to odd multiples of fex and integer multiples of fac1: 22.5 Hz (m1=1, n1=1), 17.5 Hz (m1=3, n1=2), 12.5 Hz (m1=5, n1=3), 7.5 Hz (m1=7, n1=4, and m1=13, n1=7), 2.5 Hz (m1=9, n1=5 and m1=11, n1=6), and the like.

At commercial power frequency fac2=60 Hz, as indicted by Table 1(b), as the frequency component of fluctuations that can be produced in a region lower than fex, i.e., $$f=|m2fex\pm n2fac2|$$

the following fluctuations are produced by harmonics equivalent to odd multiples of fex and integer multiples of fac2: 22.5 Hz (m2=3, n2=1), 17.5 Hz (m2=5, n2=2), 12.5 Hz (m2=7, n2=3), 7.5 Hz (m2=9, n2=4, and m2=15, n2=7), 2.5 Hz (m2=11, n2=5 and m2=13, n2=6), and the like.

In the second embodiment, the same frequency components f caused by both 50-Hz commercial power and 60-Hz commercial power are attenuated by the BEF 20. In Tables 1(l) and 1(b) with exciting frequency fex=27.5 Hz, the level at 22.5 Hz (m1=1, n1=1, m2=3, n2=1) is highest in both the cases with 50-Hz commercial power and 60-Hz commercial power.

The provision of the BEF 20 which attenuates frequency component f=22.5 Hz can realize flow rate measurement with precision increased to such an extent that no problem arises in terms of the influences of fluctuations and slurry noise caused by commercial power frequencies, and can also implement an electromagnetic flowmeter which can operated on both 50-Hz commercial power and 60-Hz commercial power at a relatively low cost without adding any new circuit arrangement.

The second embodiment has exemplified the scheme of transmitting a signal and power sharing the same signal lines, i.e., the two-wire electromagnetic flowmeter. However, the present invention is not limited to this. The present invention can also be applied to a scheme of transmitting a signal and power through different lines, e.g., a four-wire electromagnetic flowmeter, to obtain the same effects as those described above.

As has been described above, according to the present invention, a DC flow rate signal is loaded as a digital flow rate signal into the arithmetic processing section at a frequency corresponding to an integer submultiple of the differential frequency between an exciting frequency and the commercial power frequency of commercial power noise mixed in a fluid, thereby calculating a measurement flow rate. This eliminates the necessity to use any analog signal processing circuit and can efficiency suppress fluctuations in a measurement flow rate which are caused by differential noise with a relatively simple circuit arrangement at a low cost without increasing the power consumption.

In addition, the band elimination filter is provided on the output stage of the sample/hold section to attenuate the frequency components of the fluctuations contained in a DC flow rate signal whose DC potential changes in accordance with the flow velocity of a fluid, i.e., the frequency components f with the frequency component |m1fex±n1fac1| of the difference between a frequency that is an integer multiple m1 of the exciting frequency fex and a frequency that is an integer multiple n1 of the commercial power frequency fac1, and the frequency component |m2fex±n2fac2| of the difference between a frequency that is an integer multiple m2 of the exciting frequency fex and a frequency that is an integer multiple n2 of the commercial power frequency fac2. This arrangement can realize flow rate measurement with precision increased to such an extent that no problem arises in terms of the influences of fluctuations and slurry noise caused by commercial power frequencies, and can also implement an electromagnetic flowmeter which can operated on both 50-Hz commercial power and 60-Hz commercial power at a relatively low cost without adding any new circuit arrangement.

What is claimed is:

1. An electromagnetic flowmeter comprising:
   a coil which applies a magnetic field to a fluid flowing in a pipe line;
   exciting means for supplying an exciting current to said coil;
   noise eliminating means for eliminating noise from a measurement signal detected from the fluid under excitation by using a differential frequency component between a commercial power frequency and an exciting frequency; and
   arithmetic processing means for calculating a measurement flow rate on the basis of the measurement signal output from said noise eliminating means, wherein said noise eliminating means comprises:
   band elimination filter means for attenuating a component with a frequency f, of frequency components contained in a measurement signal detected from the fluid under excitation by supplying, to said coil, an exciting current with a frequency lower than both first and second commercial power frequencies used as commercial power, which satisfies $$f=|m1fex\pm n1fac1|=|m2fex\pm n2fac2|$$

where fex is an exciting frequency, fac1 is a first commercial power frequency, and fac2 is a second commercial power frequency; and
   A/D conversion means for converting an output from the band elimination filter means into a digital signal.

2. A flowmeter according to claim 1, wherein said noise eliminating means comprises:
   A/D conversion means for converting a measurement signal into a digital signal; and
   flow rate signal generating means for loading an output signal from said A/D conversion means at a frequency corresponding to an integer submultiple of a differential frequency between an exciting frequency and a commercial power frequency of commercial power noise mixed in the fluid.

3. A flowmeter according to claim 1, wherein said noise eliminating means comprises signal detection means for detecting a detection signal generated between detection electrodes provided in the pipe line.

4. A flowmeter according to claim 3, wherein the signal detection means comprises:
   amplification means for amplifying a detection signal detected from the fluid by using an exciting current supplied to said exciting means; and
   sampling means for sampling a signal output from the amplification means.

5. A flowmeter according to claim 1, wherein said arithmetic processing means comprises flow rate calculation means for calculating a flow rate by executing arithmetic processing for a flow rate signal.

6. A flowmeter according to claim 5, wherein said arithmetic processing means comprises measurement flow rate calculation means for calculating a measurement flow rate by correcting a flow rate on the basis of an adjustment coefficient corresponding an exciting current.

7. A flowmeter according to claim 6, wherein said arithmetic processing means comprises exciting current switching means for performing switching control on a current value of an exciting current on the basis of the measurement flow rate calculated by said measurement flow rate calculation means.

* * * * *